United States Patent
Wade et al.

(10) Patent No.: US 10,226,303 B2
(45) Date of Patent: Mar. 12, 2019

(54) SYSTEM AND METHOD FOR ADVANCED DATA MANAGEMENT WITH VIDEO ENABLED SOFTWARE TOOLS FOR VIDEO BROADCASTING ENVIRONMENTS

(71) Applicants: Jack Wade, La Jolla, CA (US); Chris Greve, San Diego, CA (US)

(72) Inventors: Jack Wade, La Jolla, CA (US); Chris Greve, San Diego, CA (US)

( * ) Notice: Subject to any disclaimer, the term of this patent is extended or adjusted under 35 U.S.C. 154(b) by 0 days.

(21) Appl. No.: 15/657,080

(22) Filed: Jul. 21, 2017

(65) Prior Publication Data

US 2018/0368926 A1    Dec. 27, 2018

Related U.S. Application Data

(63) Continuation-in-part of application No. 15/456,458, filed on Mar. 10, 2017, which is a continuation-in-part of application No. 15/377,817, filed on Dec. 13, 2016, application No. 15/657,080, which is a continuation-in-part of application No. 15/170,575, filed on Jun. 1, 2016, which is a continuation of application No. 14/107,329, filed on Dec. 16, 2013, now Pat. No. 9,526,586, which is a continuation of application No. 13/430,489, filed on Mar. 26, 2012, which is a continuation-in-part of
(Continued)

(51) Int. Cl.
*G06F 3/00* (2006.01)
*A61B 34/00* (2016.01)
*A61B 90/00* (2016.01)
*A61B 1/00* (2006.01)
*A61B 1/313* (2006.01)

(52) U.S. Cl.
CPC .......... *A61B 34/25* (2016.02); *A61B 1/00009* (2013.01); *A61B 1/3132* (2013.01); *A61B 90/361* (2016.02); *G06T 2200/24* (2013.01); *G06T 2207/30004* (2013.01)

(58) Field of Classification Search
CPC ..... H04L 63/1425; G06F 21/55; G06F 21/577
USPC .................................................. 710/1, 8, 38
See application file for complete search history.

(56) References Cited

U.S. PATENT DOCUMENTS

6,271,752 B1 * 8/2001 Vaios ............... G08B 13/19608
340/525
7,039,723 B2 * 5/2006 Hu ........................ G06F 3/1454
709/248
(Continued)

*Primary Examiner* — Titus Wong
(74) *Attorney, Agent, or Firm* — Olivo IP Law Group, P.C.; John W. Olivo, Jr.

(57) ABSTRACT

Video editing software tools platform utilizing a video display to provide access to specific video editing software tools, such as video oriented applications or widgets, that can assist those in a video broadcasting team, such as a camera operator or video editor, with a video broadcast feed. Various video editing software tools can provide features and functions that can add visual context to video data presented in the image stream from the video camera and provide archived information pertaining to the same. Various embodiments relate to systems and methods for simultaneously switching input image streams to output devices, while providing optional image processing functions on the image streams. Certain embodiments may enable multiple users/viewers to collaboratively control such systems and methods.

25 Claims, 4 Drawing Sheets

Related U.S. Application Data application No. 12/776,048, filed on May 7, 2010, now Pat. No. 8,266,333.

(60) Provisional application No. 61/865,037, filed on Aug. 12, 2013, provisional application No. 61/234,577, filed on Aug. 17, 2009, provisional application No. 61/182,624, filed on May 29, 2009.

(56) References Cited

U.S. PATENT DOCUMENTS

| | | | |
|---|---|---|---|
| 8,063,936 B2 * | 11/2011 | Samarasekera | G06T 15/205 348/159 |
| 8,295,649 B2 * | 10/2012 | Berini | G06K 9/00221 382/103 |
| 2002/0149617 A1 * | 10/2002 | Becker | G06F 3/1454 715/751 |

* cited by examiner

SYSTEM AND METHOD FOR ADVANCED DATA MANAGEMENT WITH VIDEO ENABLED SOFTWARE TOOLS FOR VIDEO BROADCASTING ENVIRONMENTS

PRIORITY CLAIM

This application, a continuation in part, claims the benefit of U.S. patent application Ser. No. 15/456,458, filed Mar. 10, 2017, which is a continuation in part of U.S. patent application Ser. No. 15/377,817, filed Dec. 13, 2016, which is a continuation of U.S. patent application Ser. No. 14/107,329, filed Dec. 16, 2013, and issued as U.S. Pat. No. 9,526,586 on Dec. 27, 2016, which claims the benefit of U.S. Provisional Patent Application Ser. No. 61/865,037, filed Aug. 12, 2013. This application also claims the benefit of and is a continuation in part of U.S. patent application Ser. No. 15/170,575, filed Jun. 1, 2016, which claims the benefit of Ser. No. 13/430,489, filed Mar. 26, 2012, which is a continuation-in-part of U.S. patent application Ser. No. 12/776,048, filed May 7, 2010, which claims the benefit of U.S. Provisional Patent Application Ser. No. 61/182,624, filed May 29, 2009, and 61/234,577, filed Aug. 17, 2009. Each of the foregoing applications is hereby incorporated by reference.

TECHNICAL FIELD

The technology disclosed herein relates to video editing software and, in particular, some embodiments relate to systems and methods for a software tools platform in a video editing or broadcasting environment, incorporating advanced data management.

BACKGROUND OF THE INVENTION

Video editing and broadcasting occurs with advanced audio-visual capturing technology. Still or video cameras may be used to capture image data. Video broadcast feeds are operated under a broad range of conditions and are equipped with tools to allow for streaming video, including editing tools that allow broadcasters to incorporate audio-visual content from a variety of sources. For example, a broadcast stream may be equipped with a video camera that transmits live data and can operate under a broad range of conditions. Data from these different sources are typically displayed on various display devices within the video broadcasting station. These data streams are typically transmitted using a variety of protocols and formats according to the source device and purpose of the data stream. Accordingly, a video broadcast control station typically devotes separate resources to the separate data streams.

To display visual information from data streams, large panel video and multi-screen displays are commonly employed in such contexts as Network Operations Centers (NOCs), entertainment, theaters, and retail venues. Such displays are often referred to as video walls, info walls, data walls, tiled displays, virtual walls, display walls, or virtual monitor walls. Large panel video and multi-screen displays provide groups of people with visual information that can be automatically updated, or are frequently used for enabling collaboration among viewers. Where a large panel video and multi-screen display is used for group collaboration, there is generally a requirement that the group has the ability to update and reconfigure the visual information displayed, which is usually facilitated through a video switch. Traditional video switches are controlled through a switch box and have only a single point for control access.

Video broadcasts for sporting events can identify and transmit plays in real time to a sports team fan through the fan's mobile device. This includes video data such as highlight reels, JPEGS, and collated clips. This data is also used to produce web based video, and can also be used by teams for player training and evaluations. This allows for all teams have access to video archives online to do opposing team research and player evaluations. This technology also allows for video archiving and alternative audio overlay, with the ability to record proxy video in high quality.

SUMMARY

Various embodiments of the disclosed technology provide a software platform for video editing and recording that can turn around a high-end, professional product in real time. It provides the ability to distribute video from live feeds, such as major league baseball games, as the action is still happening. The platform uses specialized data management techniques to efficiently handle incoming video data streams, making it possible to ingest, edit, log, review and distribute multiple video data streams, in multiple formats more cost effectively using commodity hardware.

Commercial broadcasting companies commonly take portions of video content and repurpose it for distribution on an Internet portal such as HBO GO or on social media platforms such as Facebook so they can reach more viewers. To do this, broadcasting companies utilize computer infrastructure that ingests live or file feeds and transcodes them into various formats -Main Screen or ABR Multi-screen-, various codec -MPEG2, H264, HEVC- and various resolutions -mobile, SD, HD, UHD. This type of real time processing typically requires vast computational resources, including a lot of expensive computer equipment. The disclosed technology includes a new approach to managing the incoming data streams which eliminates the need for temporary file storage by using an data pipe, specifically an in-memory ring buffer to feed an incoming stream to the various different encoders. Typically, these types of systems store a received data stream into a temporary file which is subsequently read by each of the various encoders. Since the process of writing and reading a file from a disk drive is relative much slower than accessing the information from computer memory, the use of the data pipe makes video stream processing many times faster.

The use of the data pipe greatly reduces the network bandwidth requirements and disk requirements and enables sustained high data rates. It also adds the ability to record video content in software without using a physical recording card. The software recorder is designed to run in a virtual machine with limited resources. Virtual machines allow multiple recorders to run simultaneously on a physical computer. This physical computer can reside anywhere on a network, not just in the traditional down-link location.

This provides broadcasters the ability to run these software recorders anywhere such as on the cloud or on their own infrastructure. Today, broadcasters typically must run recorders on blade servers which do not scale as well as cloud technology. For example, typically, a broadcaster can handle only a single feed per blade and run only a single encoder. However, using software recorders it is possible to run multiple encoders and multiple recorders per blade. This enables broadcasters to greatly expand the flexibility and the number of streams that they can record without having to vastly expand their hardware infrastructure.

Various embodiments of the disclosed technology provide a configurable live digital video recorder. Input to the recorder is a file or more commonly an RTP/TS stream with optional Forward Error Correction. Output from the recorder is a configurable mix of H.264/TS, MXF wrapped H.264, Apple ProRes, HLS segmented H.264/TS, and SCC/TTML closed captioning. All outputs can be in live mode, with a minimum of latency.

Other embodiments provide for a computer readable storage medium having instructions embedded thereon to cause a processor to perform operations similar to those described above with respect to the various systems and methods in accordance with the present invention.

These and other features, embodiments, and aspects of the present invention can be appreciated from the following drawing description and detailed description of a preferred embodiment. Other features and aspects of the disclosed technology will become apparent from the following detailed description, taken in conjunction with the accompanying drawings, which illustrate, by way of example, the features in accordance with embodiments of the disclosed technology. The summary is not intended to limit the scope of any inventions described herein, which are defined solely by the claims attached hereto.

DETAILED DESCRIPTION OF THE PREFERRED EMBODIMENT

Figure 1:
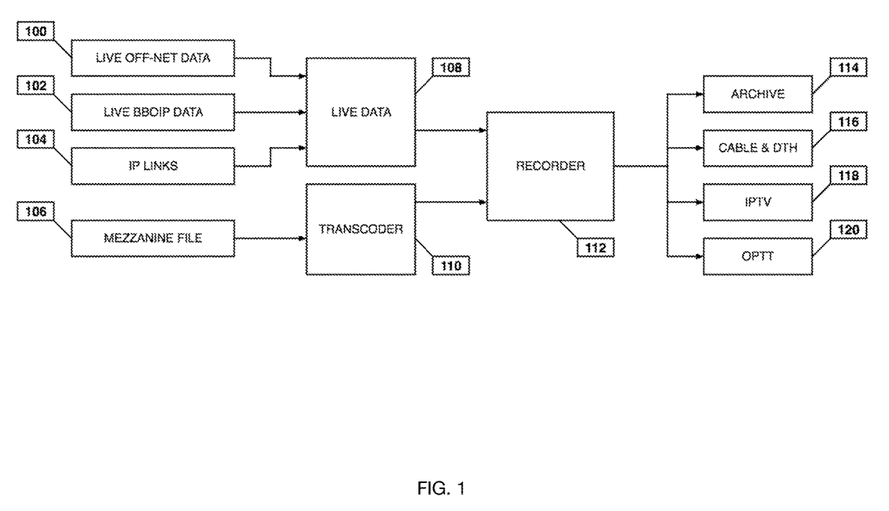
FIG. 1 is a block diagram illustrating an overview of an operating environment in which the present invention would typically be used.

FIG. 1 is a block diagram illustrating an overview of an operating environment in which the present invention would typically be used, showing data streams incoming to the system and outgoing after having been processed by the system. In accordance with the preferred embodiment of the present invention, data channels are able to transmit data to an archive 114 or content provider such as cable & direct-to-home (DTH) television 116; internet protocol television (IPTV) 118; and over-the-top (OTT) broadcasting 120 over both private and public channels. Live video data 108 is collected from live off-net 100 sources, digital internet protocol (IP) data 102, and data from online IP links 104 transmitted over an online IP network. Mezzanine files 106 is processed by the transcoder 110. The data from the live video channels 108 and the transcoder 110 is transmitted to the recorder 112. The recorder 112 stores the data streams from all channels into a cloud based online accessible archive 114, or streams the data directly to any or all of the multiple content delivery methods such as: cable & DTH 116; IPTV 118; and OTT 120.

Figure 2:
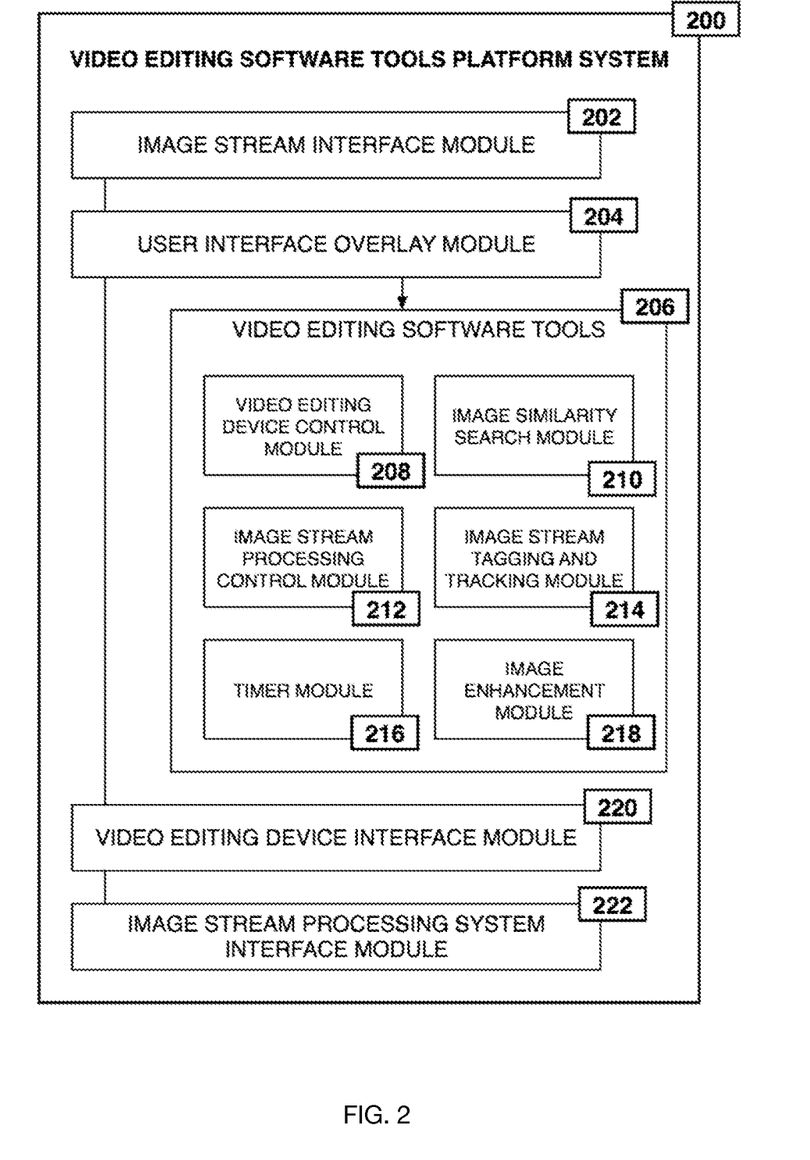
FIG. 2 is a block diagram illustrating an example of the video editing software tools platform in accordance with some embodiments of the technology described herein.

FIG. 2 is a block diagram illustrating an example of the video editing software tools platform in accordance with some embodiments of the technology described herein. The video editing software tools platform 200 provides access to applications (apps) or widgets that can assist members of the video broadcasting team during a live event. In accordance with the preferred embodiment of the present invention, the video editing software tools platform system 200 includes: an image stream interface module 202; a user interface overlay module 204; video editing software tools 206; a video editing device interface module 220; and an image stream processing system interface module 222. The image stream interface module 202 may receive an image stream acquired by a video camera or the like. Depending on the embodiment, the image stream may be received directly from the video camera, or may be provided by way of one or more components, such as an image stream processing system. The image stream received from the image stream interface module 202 may vary in resolution, frame rate, format, and protocol according to the video camera or the image stream processing system providing the image stream.

The user interface overlay module 204 may provide a user interface to the video editing software tools platform system 200, which may include one or more graphical user interface (GUI) elements presented over the image stream received through the image stream interface module 202. For some embodiments, the user interface comprises a bottom toolbar configured to be presented over the image stream, and configured to provide access to various video editing software tools 206 available through the video editing software tools platform system 200.

The video editing software tools 206 may include one or more video editing software tools, such as applications or widgets, which can be utilized with respect to the image stream being received through the image stream interface module 202. The video editing software tools 206 platform includes but is not limited to: a video editing device control module 208; an image similarity search module 210; an image stream processing control module 212; an image stream tagging and tracking module 214; a timer module 216; and an image enhancement module 218.

The video editing device interface module 220 may facilitate communication between the video editing software tools platform system 200, one or more of the video editing software tools 206, and one or more various video editing devices utilized in video broadcasting. The image stream processing system interface module 222 may facilitate communication between the video editing software tools platform system 200 and an image stream processing system utilized to process an image stream acquired by a video camera or the like. Through the communication, the image stream processing system interface module 222 may transmit control data to an image stream processing system, or receive an image stream from a video camera as processed by the image stream processing system. The image stream processing system interface module 222 may include various data interfaces, including wired or wireless network interfaces and serial communication interfaces.

Figure 3:
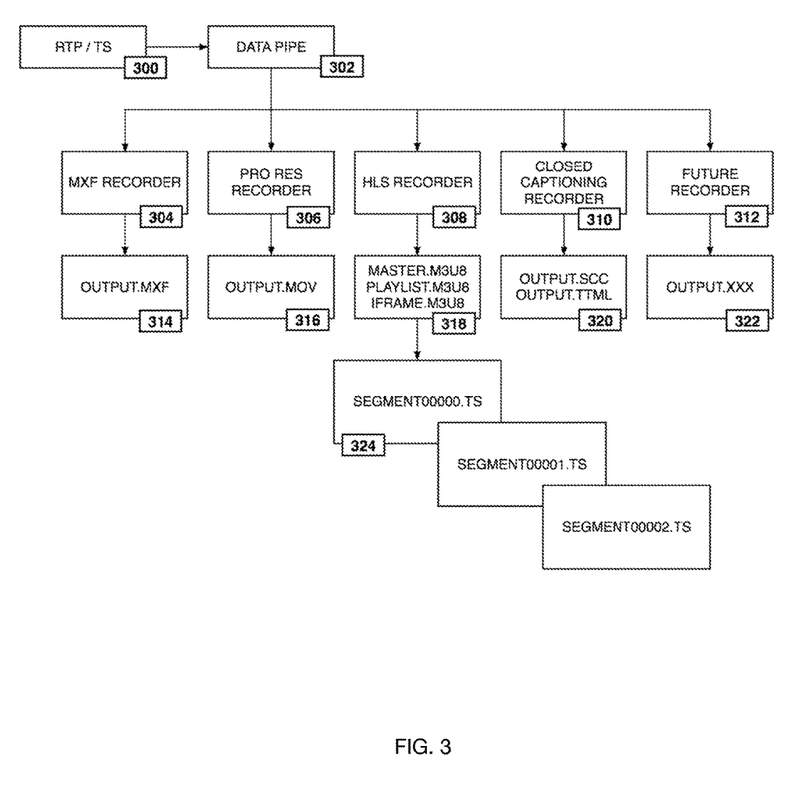
FIG. 3 is a block diagram illustrating the Real-time Transport Protocol (RTP) stream recorder program.

FIG. 3 is a block diagram illustrating the Real-time Transport Protocol (RTP) stream recorder program. In accordance with the preferred embodiment of the present invention, the RTP stream recorder is a computer program that receives an encoded digital video stream via standard internet protocols and stores and repurposes the stream in real-time on a "cloud" oriented device. The recorder can produce a wide variety of output products from the single input stream. Because the recorder has limited hardware requirements, the recorder can run on modest hardware, or multiple recorders can run simultaneously on more robust hardware. The RTP Stream Recorder reads the encoded input from an RTP broadcast source 300 with optional Forward Error Correction (FEC) and writes the packets to a Data Pipe 302. Because multicast RTP is being received over the Internet, the receiver can run "anywhere", not necessarily where the encoder is physically situated. For example, the encoded source is an 100 Mb/s AVC-I/TS stream produced by a multichannel Ateme encoder. AVC-I is an archive quality, H.264 encoded, I-frame only (no P or B frames) digital video elementary stream. The encoded source also includes up to 16 channels of MP2 audio and 2 channels of closed captioning (EIA-608/708). A transport stream (TS) 300 is the container format used to enclose each of these elements into a single stream. The RTP broadcast is received via a unicast or multicast socket. The optional FEC is a 1D or 2D column and row broadcast, where each dimension is received on separate multicast ports.

The data pipe 302 is a buffering mechanism that consumes the packets received by the RPT/TS 300 process and distributes them as needed, to each of the components in the recorder process. The data pipe removes the need for temporary disk space on the device and allows the recorder to run on limited capability hardware including virtual machines. The present invention uses data pipes, which are in-memory ring buffers, one for each of the recorder components. For example, if the recorder is configured to produce MXF 304, HLS 308 and closed captioning 310, the system would create 3 named pipes and copy the received transport stream to each. Because each of the recorder components is reading from its own data source, the component can run at its optimal rate, without having to wait for or coordinate with the other components. Other data pipes can include ProRes Recorder 306 and Future Recorder 312 data streams.

The recorder can produce a wide variety of output products. Each of the output products has unique requirements and implementation of the specific recorder component is greatly simplified by being able to read its input from its "own" data source. For example, HLS 318 requires transcoding and multiple output files 324, while MXF 304 only requires wrapping; no transcoding and a single output file 314. Some examples of output products supported are: live and closed MXF 314; Apple ProRes 316; HLS with master and IFrame playlists 318; SCC and TTML closed captioning 320; and future recorded output 322.

Figure 4:
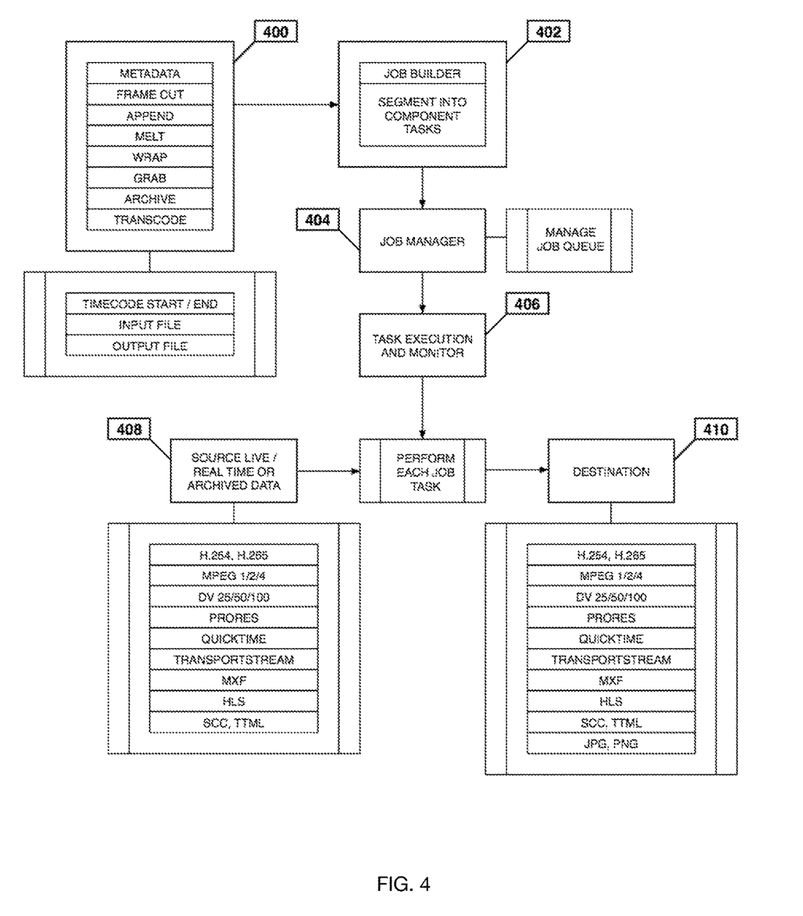
FIG. 4 is a block diagram illustrating the Digital Scissors Services Oriented Architecture.

FIG. 4 is a block diagram illustrating the Digital Scissors Services Oriented Architecture. In accordance with the preferred embodiment of the present invention, Digital Scissors is a Service Oriented Architecture (SOA) that provides for the manipulation of digital video files. Commands are sent to the service requesting an action be performed upon a source and potentially producing an output. A command 400 is created by an external process requesting an action by the service. A command 400 can be an XML document describing the action, a REST API request or a direct library call. Commands include: Cut a timecode range from a source 408 to a destination 410; Grab 1 or more frames from a source 408 with a specified timecode signature to destination(s) 410; Transcode change the essence or container of a source 408 to a different essence or container. For example, H.264/TS to MPEG4; Melt is the process of trimming the preamble and post-amble of a recording; Append a timecode range from a source file 408 onto a destination 410; Wrap a source essence with a container format to a destination 410; Metadata-Info provides the information about the underlying digital video: frame size, bitrate, format, color space and the like; and Archive 408 is the near-line storage of archived sources and clips.

The commands 400 use SMPTE timecode to identify which frame or of range frames is being requested. Timecode is generally present in the digital video source material and make it possible for all observers to reference the same frame. Timecode is what makes frame accurate identification possible. An example XML command to request the cutting a source file to a destination using a timecode range is:

```
<cut>
  <in>
    <file>/damsamfs1/team1-team2.dv</file>
    <timecode>
      <start>10:20:22.00</start>
      <end>10:20:32.00</end>
    </timecode>
    <granularity>frame-accurate</granularity>
  </in>
  <out>
    <overwrite>false</overwrite>
    <append>false</append>
    <file>/damsamfs1/gclips/team1-team2-clip1.dv</file>
  </out>
</cut>
```

The Job Builder 402 coalesce all requests into a queue of jobs that are executed in parallel but at a configured maximum rate. Invalid requests are immediately reported to the requestor. Requests are received from multiple clients and in multiple forms. Each request creates a new Job, the request is parsed and validated. The Job Builder 402, then creates an internal list of tasks needed to accomplish the request and adds them to the Job. The Job is placed in a queue ready for execution by the Job Manager 404.

The Job Manager 404 processes the Job Queue and executes ready Jobs in parallel at a configured maximum rate. There are many design tradeoffs that are configurable within the Job Manager. For example, does the request want priority execution; should the manager try to minimize load, memory use or time. Generally, Jobs will have many tasks that are needed to accomplish the requested action. Tasks within the Job may be required to execute sequentially. Certain tasks may be able to run in parallel. For example, a task to transcode a clip that was created during a cutting task will have to execute sequentially. Each task is executed and monitored 406 for failure. When the Job is complete, the result is reported to the requestor. Each task is specialized and designed to accomplish a specific action by the task execution and monitor 406. For example, there are cutting, grabbing, metadata, transcode, and wrapping tasks. And each of those tasks as specific versions to handle the following formats: H.264, H.265; MPEG 1/2/4; DV 25/50/100; Apple ProRes; QuickTime; MPEG Transport Streams; MXF; HLS, M3U8; and SCC, TTML. Tasks are specific to the action being requested. Each of these tasks has specialized versions, depending on the input or output format being requested. A task that is cutting a DV100 file has different requirements from a task cutting an MP4 file. Searching for timecode is also different for each of the formats, H.264/TS has timecode encoded into every frame, where MXF just has a start timecode in the header of the file.

Some formats, like AVC-I/MXF, ProRes and DV100 directly support frame accurate cutting or grabbing. H.264/TS is much harder. As an example, this is an algorithm to support frame accurate cutting of H.264/TS: Find the TS packet at which the clip starting time-code occurs. This will be the frame-accurate cut point. From the frame accurate cut point, seek FORWARD in the stream until an I-frame (FWD IFRAME). If the clip starting time-code happens to fall on an I-frame then it is not necessary to seek forward. Create the tail clip that includes all video/audio data from this I-frame up to the frame-accurate frame that occurs at the clip ending time-code. If the clip starting time-code happened to fall on an I-frame, then the tail clip is the final frame-accurate clip and the process is finished. From the frame accurate cut point, find the audio frame that synchronizes with the frame accurate cut point video frame. Create the audio-only audio-head clip that contains all audio data from this point up to I-frame FWD IFRAME. From the frame-accurate cut point, seek REVERSE in the stream until an I-frame (REV IFRAME) encountered. Create the video-only video-head-Itol clip that contains all video data from this point up to I-frame FWD IFRAME. Note that this video-head-Itol clip should contain exactly 60 frames since this is what Inlet uses as the period (2 seconds) between successive I-frames. Using the FFMPEG application, transcode the video-head-Itol clip into a raw YUV 4:2:2 video frame file (YUV RAW). This will give full video data for each frame in the video-head-Itol clip. Note that in this process, all video-head-Itol clip timing information is lost. Calculate the number of frames to drop from the head of the YUV RAW file and create the frame-accurate raw YUV 4:2:2 video frame file (YUV FA). Using the FFMPEG application, transcode the YUV FA frame-accurate raw YUV 4:2:2 video frame file into a video-only H.264 transport stream video-head clip. Note that this video-head clip will contain <60 video frames. Change the PTS timestamps in the video-head clip so that they match the corresponding PTS timestamps as they appear in the source video. Recall that the transcoding from timestamped transport stream to YUV RAW removed all timing information. The transcoding of the YUV RAW to YUV FA reapplies timing information, however, this timing information is based at time zero whereas the associated audio clip is timestamped with the original timing data as it appears in the source video. Append the audio-head clip to the video-head clip to create the frame accurate head clip that includes all video/audio data from the frame-accurate cut point to FWD IFRAME. Append the tail clip to the head clip to create the final complete frame-accurate clip.

While various embodiments of the disclosed technology have been described above, it should be understood that they have been presented by way of example only, and not of limitation. Likewise, the various diagrams may depict an example architectural or other configuration for the disclosed technology, which is done to aid in understanding the features and functionality that may be included in the disclosed technology. The disclosed technology is not restricted to the illustrated example architectures or configurations, but the desired features may be implemented using a variety of alternative architectures and configurations. Indeed, it will be apparent to one of skill in the art how alternative functional, logical or physical partitioning and configurations may be implemented to implement the desired features of the technology disclosed herein. Also, a multitude of different constituent module names other than those depicted herein may be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the disclosed technology is described above in terms of various exemplary embodiments and implementations, it should be understood that the various features, aspects and functionality described in one or more of the individual embodiments are not limited in their applicability to the particular embodiment with which they are described, but instead may be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, may be combined in a single package or separately maintained and can further be distributed in multiple groupings or packages or across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives may be implemented without confinement to the illustrated examples. For example, block diagrams and their accompanying description should not be construed as mandating a particular architecture or configuration.

What is claimed is:

1. A system for switching an image stream input to an image stream output, comprising:
   an image stream input interface;
   an image stream output interface;
   a first image processing module configured to accept an image stream from the image stream input interface or another image processing module, apply an image processing function to the image stream, and output a processed image stream;
   a second image processing module; and
   a switching matrix in communication with the image stream input interface, the image stream output interface, the first image processing module, and the second image processing module, wherein the switching matrix is configured to:

selectively map the image stream input interface to the image stream output interface or to the first image processing module, selectively map the processed image stream from the first image processing module to the image stream output interface or to the second image processing module, a ring buffer suitable for reducing network bandwidth requirements for recording said image stream without the use of a physical recording card and said ring buffer is sized sufficiently to facilitate recording said image stream for allowing multiple recorders to run simultaneously on a physical computer of a size wherein said size is minimized corresponding with said image stream requirements, and a cloud or hosted local data platform providing broadcasters with a software recorder for recording said image stream without need for a non-software recorder corresponding with said software recorder enabling said broadcasters greater video handling capacity per a fixed amount of computer capacity.

2. The system of claim 1, further comprising a data input interface, wherein the switching matrix is further in communication with the data input interface such that the switching matrix can further selectively map the data input interface to the image stream output interface or to the first image processing module.

3. The system of claim 2, wherein the image stream input interface comprises the data input interface.

4. The system of claim 1, wherein the switching matrix can selectively map the image stream input interface or the processed image stream in real-time.

5. The system of claim 1, wherein the switching matrix can selectively map the image stream input interface to more than one image processing module or to more than one image stream output interface simultaneously.

6. The system of claim 1, wherein the switching matrix can selectively map the processed image stream to more than one image processing module or to more than one image stream output interface simultaneously.

7. The system of claim 1, wherein the switching matrix can selectively map the image stream input interface or the processed image stream based on a criterion.

8. The system of claim 7, wherein the criterion relates to source or content of the image stream input interface or the processed image stream.

9. The system of claim 7, wherein the criterion for the processed image stream relates to results of a preceding image processing module.

10. The system of claim 1, wherein the image processing module can process a plurality of image streams in parallel.

11. The system of claim 1, wherein the image stream input interface or image stream output interface has a Digital Video Interface (DVI) connector, High-definition Multimedia Interface (HDMI) connector, a Bayonet Neill-Concelman (BNC) connector, a fiber optic connector, a DisplayPort connector, a Universal Serial Bus (USB) connector, or a Firewire (IEEE1394) connector.

12. The system of claim 1, wherein the image stream input interface is configured to convert from or the image stream output interface is configured to: a Digital Video Interface (DVI) standard, a High-definition Multimedia Interface (HDMI) compatible standard, a Red-Green-Blue (RGB) Analog standard, a Red-Green-Blue (RGB) Digital standard, a DisplayPort standard, a National Television System Committee (NTSC) standard, a Phase Alternate Line (PAL) standard, or a Serial Digital Interface (SDI) standard.

13. The system of claim 1, wherein the system comprises a plurality of image processing modules.

14. The system of claim 1, wherein the system comprises a plurality of image stream input interfaces.

15. The system of claim 1, wherein the system comprises a plurality of image stream output interfaces.

16. The system of claim 1, wherein the image processing function comprises an image stream mix function, an image stream scale function, an image stream blend function, an image stream encoding algorithm, or an image stream enhancement function.

17. The system of claim 1 wherein the image stream input interface is configured to receive the image stream from an image stream capture device, an image stream playback device, a computer system, or a sensor device.

18. The system of claim 1, wherein the image stream output interface is configured to output to a display, a computer system, or recording device.

19. The system of claim 1, wherein the system is configured to output an image stream through a virtual display.

20. The system of claim 1, further comprising a control interface through which a user can operate the system, configure the system, or check status of the system.

21. A method for switching an image stream input to an image stream output, comprising:

receiving an original image stream from an image stream input interface;

receiving a first processed image stream from a first image processing module, wherein the first image processing module generates the first processed image stream by applying a first image processing function to an image stream;

using a switching matrix to selectively map the original image stream to:

a second image processing module, wherein the second image processing module is configured to receive the original image stream from the switching matrix, apply a second image processing function to the original image stream, and output a second processed image stream, or an image stream output interface; and using the switching matrix to selectively map the first processed image stream to:

the second image processing module, wherein the second image processing module is further configured to receive the first processed image stream from the switching matrix, apply the second image processing function to the first processed image stream, and output a third processed image stream, or the image stream output interface, a ring buffer processor suitable for reducing network bandwidth requirements for recording said image stream without the use of a physical recording card and said ring buffer is sized sufficiently to facilitate recording said image stream for allowing multiple recorders to run simultaneously on a physical computer of a size wherein said size is minimized corresponding with said image stream requirements, and a cloud or hosted local data platform processor providing broadcasters with a software recorder for recording said image stream without need for a non-software recorder corresponding with said software recorder enabling said broadcasters greater video handling capacity per a fixed amount of computer capacity.

22. The method of claim 21, wherein when the switching matrix selectively maps the original image stream to the second image processing module, the method further comprises using the switching matrix to selectively map the second processed image stream to a third image processing module.

23. The method of claim 21, wherein the switching matrix selectively maps the image stream input interface to more than one image processing module or to more than one image stream output interface simultaneously.

24. The method of claim 21, wherein the switching matrix selectively maps the processed image stream to more than one image processing module or to more than one image stream output interface simultaneously.

25. The method of claim 21, wherein the switching matrix selectively maps the image stream input interface or the processed image stream based on a criterion implemented through the control interface.

* * * * *